(12) United States Patent
Tanaka et al.

(10) Patent No.: US 10,105,061 B2
(45) Date of Patent: Oct. 23, 2018

(54) SUBJECT INFORMATION OBTAINING APPARATUS

(71) Applicant: CANON KABUSHIKI KAISHA, Tokyo (JP)

(72) Inventors: Takatoshi Tanaka, Tokyo (JP); Naoto Abe, Machida (JP)

(73) Assignee: Canon Kabushiki Kaisha, Tokyo (JP)

(*) Notice: Subject to any disclaimer, the term of this patent is extended or adjusted under 35 U.S.C. 154(b) by 500 days.

(21) Appl. No.: 14/469,368

(22) Filed: Aug. 26, 2014

(65) Prior Publication Data

US 2015/0119680 A1  Apr. 30, 2015

(30) Foreign Application Priority Data

Oct. 31, 2013  (JP) ................................ 2013-227240

(51) Int. Cl.
  *A61B 5/00* (2006.01)
  *A61B 8/08* (2006.01)
  *A61B 8/13* (2006.01)
  *A61B 6/04* (2006.01)
  *A61B 8/00* (2006.01)

(52) U.S. Cl.
  CPC ............ *A61B 5/0095* (2013.01); *A61B 5/708* (2013.01); *A61B 8/0825* (2013.01); *A61B 8/13* (2013.01); *A61B 8/4461* (2013.01); *A61B 8/4494* (2013.01); *A61B 8/469* (2013.01); *A61B 6/0435* (2013.01); *A61B 8/406* (2013.01); *A61B 8/5207* (2013.01); *A61B 8/54* (2013.01)

(58) Field of Classification Search
  CPC ......... A61B 5/0095; A61B 5/708; A61B 8/13; A61B 8/469; A61B 8/4494; A61B 8/4461; A61B 8/0825; A61B 8/54; A61B 8/5207; A61B 8/406; A61B 6/0435
  See application file for complete search history.

(56) References Cited

U.S. PATENT DOCUMENTS

| 4,167,180 A | 9/1979 | Kossoff |
| 6,104,942 A | 8/2000 | Kruger |
| 6,216,025 B1 | 4/2001 | Kruger |

(Continued)

FOREIGN PATENT DOCUMENTS

| CN | 103354731 A | 10/2013 |
| CN | 103476327 A | 12/2013 |

(Continued)

*Primary Examiner* — Peter Luong
(74) *Attorney, Agent, or Firm* — Canon USA, Inc. I.P. Division

(57) ABSTRACT

A long period of time is required to complete measurement performed by a subject information obtaining apparatus. Accordingly, a subject information obtaining apparatus includes a receiver including a plurality of conversion elements which receive acoustic waves and output reception signals and a supporting member including the conversion elements disposed therein, a movement mechanism configured to move the receiver, and a controller configured to input a driving signal to the movement mechanism. The conversion elements are disposed in the supporting member such that directional axes of a number of the conversion elements are converged. The controller controls the movement mechanism so that a center position of a scanning trajectory of the receiver is changed.

21 Claims, 13 Drawing Sheets

(56) References Cited

U.S. PATENT DOCUMENTS

| | | | | |
|---|---|---|---|---|
| 6,574,499 B1 | * | 6/2003 | Dines | .................... A61B 6/0414 |
| | | | | 128/915 |
| 6,633,774 B2 | | 10/2003 | Kruger | |
| 2004/0100503 A1 | * | 5/2004 | Morita | .................... A61B 6/463 |
| | | | | 715/804 |
| 2010/0016717 A1 | | 1/2010 | Dogra | |
| 2010/0036240 A1 | * | 2/2010 | Ismail | ...................... A61B 5/05 |
| | | | | 600/425 |
| 2010/0177866 A1 | * | 7/2010 | Shibuya | ................. A61B 6/032 |
| | | | | 378/20 |
| 2011/0306865 A1 | | 12/2011 | Thornton | |
| 2013/0217995 A1 | | 8/2013 | Kruger | |
| 2013/0310690 A1 | * | 11/2013 | Chang | ..................... A61B 8/08 |
| | | | | 600/443 |

FOREIGN PATENT DOCUMENTS

| | | | |
|---|---|---|---|
| EP | 2148183 A1 | 1/2010 | |
| JP | S55-500499 A | 8/1980 | |
| JP | 2005-040301 A | 2/2005 | |
| JP | 4341987 B2 | 10/2009 | |
| JP | 2011-229620 A | 11/2011 | |
| JP | 2012-179348 A | 9/2012 | |
| WO | 99/58957 A1 | 11/1999 | |
| WO | 2012/108170 A1 | 8/2012 | |
| WO | 2012/108172 A1 | 8/2012 | |
| WO | WO2012/108172 * | 8/2012 | ............... A61B 8/00 |
| WO | 2013/082586 A2 | 6/2013 | |

* cited by examiner

SUBJECT INFORMATION OBTAINING APPARATUS

BACKGROUND OF THE INVENTION

Field of the Invention

The present invention relates to a subject information obtaining apparatus. Specifically, the present invention relates to a photoacoustic apparatus which measures acoustic waves generated due to a photoacoustic effect. Examples of the photoacoustic apparatus include a photoacoustic apparatus used for observing a breast portion of a living body.

Description of the Related Art

In recent years, diagnosis apparatuses employing photoacoustic tomography (PAT) using a photoacoustic effect have been developed. Such an apparatus generates and displays an image by irradiating illumination light (near infrared light) of a Nd:YAG laser pulse light source on a subject and receiving acoustic waves generated due to a photoacoustic effect in the subject using a two-dimensionally or three-dimensionally-arrayed conversion elements (transducers).

As an example of general photoacoustic apparatuses, Japanese Patent No. 4341987 discloses an apparatus for observing an inside of a subject. A portion to be examined is inserted into a recess of the apparatus and a receiver including conversion elements circularly performs scanning on the subject and a portion in the vicinity of the subject.

SUMMARY OF THE INVENTION

In a subject information obtaining apparatus, when a subject or a portion to be examined is changed, a position of a region from which information is to be obtained relative to the apparatus is changed. For example, in general, in a breast cancer diagnosis, a region including a breast and a portion called an axilla positioned below an armpit is to be observed by an operator (refer to FIG. 3). Accordingly, shapes and centers of regions from which the operator obtains information in right and left breasts are different from each other. When a case where the right breast is observed is compared with a case where the left breast is observed, centers of respective information obtaining regions are shifted from each other in a lateral direction. However, since a rotation center of a scanning trajectory of a receiver is fixed in the apparatus disclosed in Japanese Patent No. 4341987, a large information obtaining region is designed in advance taking difference between the information obtaining regions of the right and left breasts into consideration so that both the information obtaining regions are covered. Consequently, there arises a problem in that a long period of time is required for completing measurement.

Accordingly, the present invention provides a subject information obtaining apparatus including a receiver including a plurality of conversion elements which receive acoustic waves and output reception signals and a supporting member including the conversion elements disposed therein, a movement mechanism configured to move the receiver, and a controller configured to input a driving signal to the movement mechanism. The conversion elements are disposed in the supporting member such that directional axes of a number of the conversion elements are converged. The controller controls the movement mechanism so that a center position of a scanning trajectory of the receiver is changed.

Further features of the present invention will become apparent from the following description of exemplary embodiments with reference to the attached drawings.

DESCRIPTION OF THE EMBODIMENTS

Embodiments of the present invention will be described hereinafter with reference to the accompanying drawings. Note that the present invention is not limited to these as long as techniques do not depart from the scope of the present invention.

In this specification, a term "scanning of a receiver" includes movement of a receiver while the receiver receives acoustic waves and movement of the receiver while the receiver does not receive acoustic waves. Furthermore, in this specification, a term "measurement" means reception, by a receiver, of acoustic waves generated in a subject. Moreover, in this specification, a term "scanning trajectory" represents a trajectory of positions of the receiver which is moved during measurement. A term "center of a scanning trajectory" represents a center of gravity of a region formed by tracing outer periphery of a scanning trajectory. In this specification, a term "subject information obtaining region" represents a region in which subject information is generated based on reception signals of acoustic waves.

Furthermore, in this specification, examples of the subject information include initial sound pressure distribution of acoustic waves, optical energy absorption density distribution, absorption coefficient distribution, and distribution of concentration of a substance constituting the subject. Examples of the concentration of a substance include saturation of oxygen, concentration of oxyhemoglobin, concentration of deoxyhemoglobin, and total concentration of hemoglobin. The term "total concentration of hemoglobin"

represents a sum of the concentration of oxyhemoglobin and the concentration of deoxyhemoglobin.

First Embodiment

Figure 1:
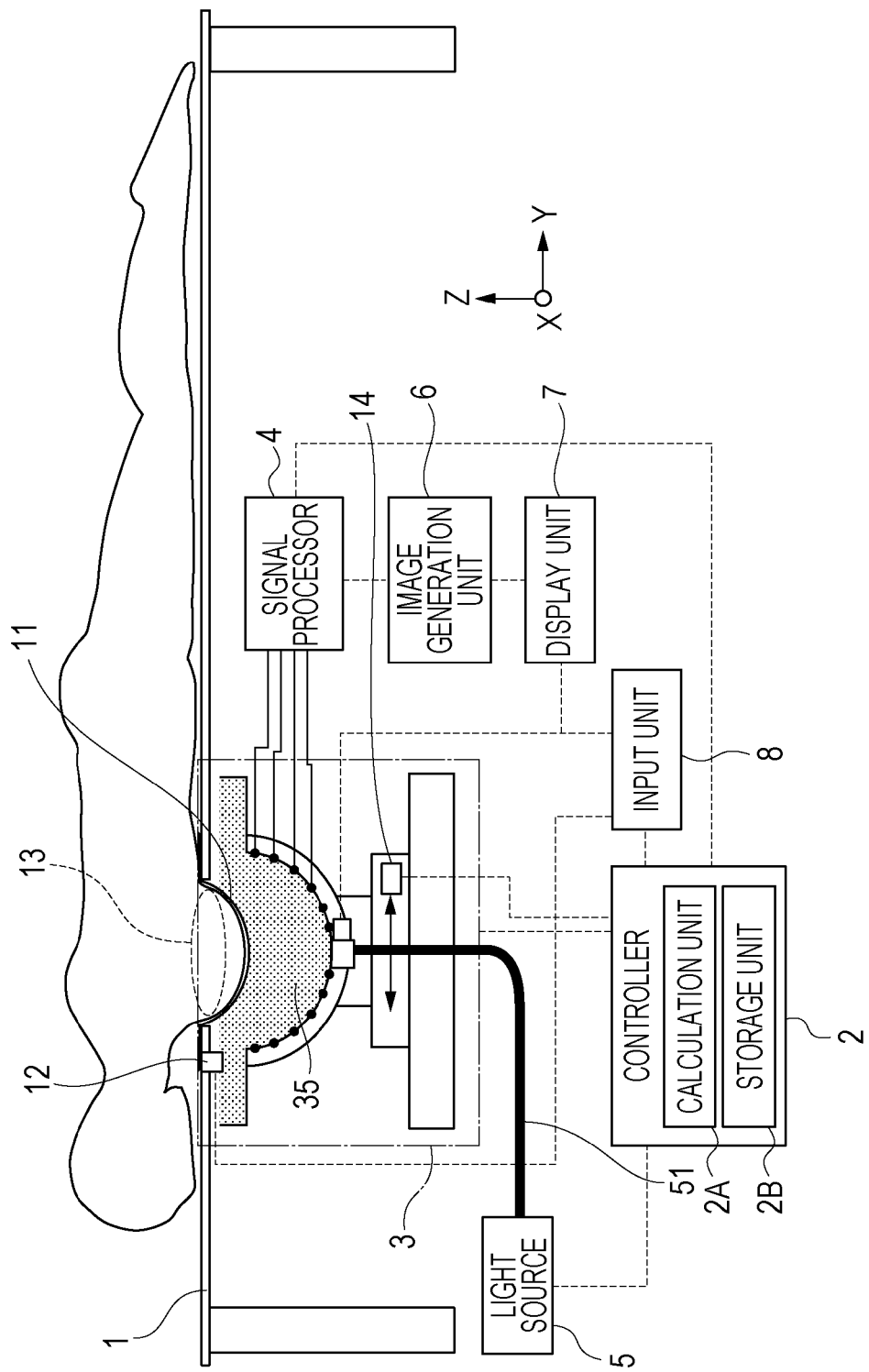
FIG. 1 is a conceptual diagram illustrating a subject information obtaining apparatus.

FIG. 1 is a diagram schematically illustrating a subject information obtaining apparatus. In this embodiment, a subject information obtaining apparatus which moves a receiver so as to receive acoustic waves from a breast which is a portion to be examined will be described as an example. An examinee (a subject) in a prone position on a bed 1 which is a subject supporting unit inserts a breast protruding downward which is a portion to be examined to a breast insertion opening 13 (an opening). In the breast insertion opening 13, a holding member 11 (an examination portion holding member) which holds the breast is disposed. An examination portion detector 12 (a target breast detector) is disposed in a portion where the bed 1 and the holding member 11 contact with each other, and the examination portion detector 12 obtains information on a type (right or left, for example) of breast which is a target of the subject information obtainment.

A controller 2 controls methods for controlling a reception unit 3, a signal processor 4, an image generation unit 6, and a display unit 7 in accordance with an input from an input unit 8 (a target breast input unit). The controller 2 sets a center position of a scanning trajectory in accordance with information input from the input unit 8. The controller 2 may further set a subject information obtaining region in accordance with the information input from the input unit 8.

The signal processor 4 performs AD conversion on a reception signal of a received acoustic wave so as to generate a digitalized reception signal. The image generation unit 6 generates a 2D or 3D photoacoustic image in accordance with the reception signal and displays the generated photoacoustic image in the display unit 7.

Note that the image generation unit 6 may obtain subject information by performing a process based on an image reconstruction algorithm on the reception signal. Examples of the image reconstruction algorithm for obtaining subject information include backprojection in a time domain or a Fourier domain generally used in a tomography technique. When a long period of time may be used for the reconstruction, an image reconstruction method such as an inverse problem analysis method performed by a repetition process may be used.

In this specification, the term "processor" conceptually includes the signal processor 4 and the image generation unit 6. A calculation unit of the signal processor 4 or the image generation unit 6 typically includes elements including a CPU, a GPU, and an A/D converter and circuits including an FPGA and an ASIC. Note that the calculation unit may include a single element and a single circuit or may include a plurality of elements and a plurality of circuits. Furthermore, processes may be performed by any element or any circuit.

The subject information obtaining apparatus of this embodiment consecutively measures right and left breasts. An operator inputs information on a type, a position, a shape, and the like of a breast as information on a portion to be examined using the input unit 8 before measurement is performed. The controller 2 may obtain the information on a type, a position, a shape, and the like of a breast using a result of detection performed by the examination portion detector 12. Furthermore, the controller 2 may use a setting value corresponding to a type of breast which is stored in advance in a storage unit included in the controller 2. For example, in a case where information on the portion to be examined in one of the right and left breasts, that is, a first breast, has been input by the operator, when the other one of the breasts, that is, a second breast, is to be measured, the controller 2 may use a setting value corresponding to the first breast stored in the storage unit included in the controller 2 in advance. In this case, information on the portion to be examined in the second breast is automatically set by the controller 2. Furthermore, when the type of breast is input by the operator, the controller 2 may obtain information on the other portion to be examined corresponding to the input breast type which is stored in the storage unit of the controller 2 in advance.

The input unit 8 inputs information on a portion to be examined to the controller 2. The operator may directly input the information to the input unit 8 by means of an input button (not illustrated), a mouse, a keyboard, or the like, for example. Moreover, the input unit 8 may automatically input the type of portion to be examined (a target breast) by inputting an output of the examination portion detector 12. With these configurations, the operator is not required to directly input a type of breast, and wrong examination portion information generated by an input error of the operator is prevented from being obtained. Furthermore, the input unit 8 allows the operator to directly input information (a manual input mode) and also allows input of an output of the examination portion detector 12 (an automatic input mode), and the two modes may be switched from one to another.

The examination portion detector 12 (a target examination portion detector) transmits an electric signal which is uniquely output depending on a shape, a position, and the like of the holding member 11 or a portion to be examined (the breast of the examinee in this embodiment) detected by a mechanical unit, an electric unit, or an optical unit, for example, to the controller 2. In the detection by a mechanical unit, a protrusion is formed on the holding member 11 and a determination as to whether a microswitch is turned on or off so that a type of the holding member 11 is determined. In the detection by an electric unit, an electric contact is formed on the holding member 11 and it is determined whether the electric contact is in a contact state and in a conductive state. In the detection by an optical unit, the holding member 11 or a type of breast of an examinee is detected using a camera image.

The holding member 11 (an examination portion holding member) holds a portion to be examined. In this embodiment, the holding member 11 has a bowl shape so as to easily hold the portion to be examined (a breast in this embodiment). A perfect spherical surface is not required but a shape which matches shapes of the breast and an axilla is used. A plurality of supporting members 11 having different shapes for right and left breasts and having different sizes corresponding to breast sizes are preferably provided.

The holding member 11 is thin (0.1 to 0.5 mm) so as to easily transmit ultrasonic waves, is a transparent member which transmits light, and is a member having intensity sufficient for a weight of the examinee. As a material of the holding member 11 having such characteristics, polyethylene terephthalate (PET) is preferably used.

The holding member 11 may be deformed in accordance with a shape of a portion to be examined. For example, a member having a sheet shape formed by a material having a Young's modulus smaller than a Young's modulus of a typical breast may be used for the holding member 11.

A portion between the holding member 11 and a breast is preferably filled with an adjustment member (not illustrated)

so that ultrasonic waves are easily transmitted. Examples of the adjustment member include water and gel.

A light source 5 supplies light energy to a portion to be examined (a breast, for example) of a subject so that acoustic waves are generated. When the subject is a living body, the light source 5 emits light having a specific wavelength to be absorbed by a specific one of constituents of the living body. For example, the light source 5 emits near infrared light to the portion to be examined. The light source 5 may be provided integrally with the photoacoustic apparatus of this embodiment or may be provided separately from the photoacoustic apparatus.

As a light source, a pulse light source capable of generating pulse light of several nanoseconds order to several hundreds nanoseconds order as irradiation light is preferably used. Specifically, to effectively generate acoustic waves, a pulse width of approximately 10 to 100 nanoseconds is used. A laser is preferably used as the light source since high output is obtained. However, a light emitting diode may be used instead of the laser. As the laser, various lasers including a solid-state laser, a gas laser, a fiber laser, a dye laser, and a semiconductor laser may be used. A timing, a waveform, intensity, and the like of irradiation are controlled by a light source controller, not illustrated. In the present invention, as a wavelength of a light source to be used, a wavelength for propagating light to an inside of a breast is preferably used. Specifically, the wavelength of 500 nm or more to 1200 nm or less is preferably used.

Figure 2:
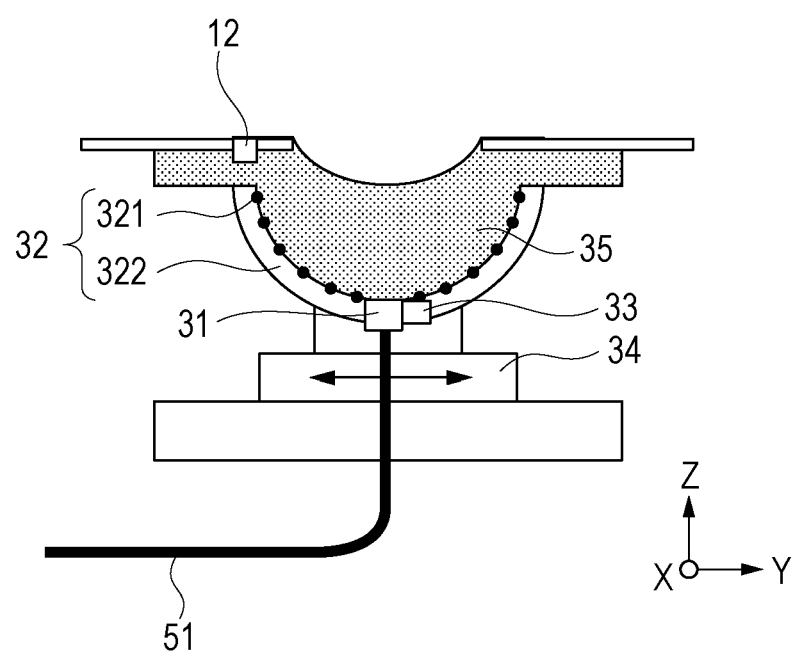
FIG. 2 is a conceptual diagram illustrating a reception unit of the present invention.

FIG. 2 is a diagram schematically illustrating the reception unit 3 of the present invention. The reception unit 3 includes a light irradiation unit 31 which irradiates pulse light supplied from the light source 5 and guided by a light guiding unit 51 to a breast, a receiver 32 which receives acoustic waves (ultrasonic waves) generated by the breast, and a camera 33 used to observe a state of supporting of the breast. The reception unit 3 further includes a movement mechanism 34 which moves the light irradiation unit 31, the receiver 32, and the camera 33. The light irradiation unit 31 is located in a position which confronts the breast, for example, and irradiates pulse light to the breast. The receiver 32 receives photoacoustic waves generated due to thermal expansion. A portion between the receiver 32 and the holding member 11 is filled with an adjustment member 35. As the adjustment member 35, water having an acoustic impedance which is more similar to that of a human body when compares with an acoustic impedance of air is used.

The receiver 32 includes a plurality of conversion elements 321 which receive acoustic waves and a supporting member 322 (conversion element supporting member) in which the conversion elements 321 are disposed. Typically, receiving sensitivity is highest in normal directions of reception surfaces of the conversion elements 321, and as an incident angle becomes large, the receiving sensitivity becomes low. In this specification, axes along directions in which the receiving sensitivity of the conversion elements 321 is highest are referred to as "directional axes". In the receiver 32 of this embodiment, the conversion elements 321 which receive photoacoustic waves are disposed on the supporting member 322 such that reception surfaces of at least a number of the conversion elements 321 have different angles. In this embodiment, the conversion elements 321 are disposed on the supporting member 322 such that at least a number of the directional axes are converged.

The conversion elements 321 are disposed on the supporting member 322 such that directions of high receiving sensitivity of a number of the conversion elements 321 are different from directions of high receiving sensitivity of the others of the conversion elements 321 and the directions of the high receiving sensitivity of the number of the conversion elements 321 direct a certain region. Here, as for the certain region, the conversion elements 321 may receive acoustic waves generated from the certain region more sensitively when the directions of high receiving sensitivity of the conversion elements 321 direct the certain region when compared with a case where the directions of high receiving sensitivity are parallel to one another.

By this, resolution of an image of the certain region generated in accordance with acoustic waves generated from the certain region becomes higher when compared with the case where the directions of high receiving sensitivity are parallel to one another.

Accordingly, the conversion elements 321 at least include first and second conversion elements which are disposed on the supporting member 322 such that directions of high receiving sensitivity of the first and second conversion elements are different from each other (non-parallel) and direct to the certain region.

Furthermore, the conversion elements 321 may at least include first and second conversion elements which are disposed on the supporting member 322 such that directions of highest receiving sensitivity of the first and second conversion elements are different from each other and direct to the certain region. Specifically, the conversion elements 321 may be disposed on the supporting member 322 such that directions of highest receiving sensitivity of a number of the conversion elements 321 are different from directions of highest receiving sensitivity of the others of the conversion elements 321 and the directions of the highest receiving sensitivity of the number of the conversion elements 321 direct the certain region. Here, as for the certain region, the conversion elements 321 may receive photoacoustic waves generated from the certain region more sensitively when the directions of highest receiving sensitivity of the conversion elements 321 direct the certain region when compared with the case where the direction of highest receiving sensitivity are parallel to each other.

Since the conversion elements 321 are disposed as described above, the receiving sensitivity of the receiver 32 relative to acoustic waves generated from the certain region may be enhanced. By this, resolution of an image of the certain region generated in accordance with acoustic waves generated from the certain region may be enhanced when compared with the case where the directions of highest receiving sensitivity are parallel to each other.

Since the directions of receiving sensitivity of the conversion elements 321 higher than a certain level are directed to the certain region, high resolution of an image corresponding to the region may be obtained. In this specification, the region capable of performing reception of high sensitivity is referred to a "high sensitivity region" which consequently corresponds to a high resolution region. In this embodiment, the high resolution region represents a range from a point of highest resolution to a point of half of the highest resolution. Specifically, a diameter r in Expression (1) below represents a diameter of the high resolution region.

$$r = \frac{r_0}{\phi_d} \cdot \sqrt{(R^2 - R_H^2)} \tag{1}$$

Here, "R" represents allowable resolution, "$R_H$" represents highest resolution, $r_0$ represents a diameter of a ball in which a sound detection element is disposed, and $\Phi_d$ represents a diameter of the first conversion element. Here, the allowable resolution represented by "R" corresponds to half of the highest resolution.

The conversion elements 321 receive acoustic waves and convert the acoustic waves into analog electric signals. In this specification, the term "reception signal" includes analog signals output from the conversion elements 321 and digital signals obtained by AD conversion. Any element may be used such as conversion elements (transducers) using a piezoelectric phenomenon, conversion elements using optical resonance, and conversion elements using capacity change, as long as acoustic waves are detected. In this embodiment, the conversion elements 321 are disposed in the receiver 32. Use of such elements arranged in a multi-dimensional manner enables simultaneous reception of acoustic waves in a plurality of locations and attains reduction of a reception time. For example, the conversion elements 321 are disposed in a 3D spiral manner along with an inner surface of a hemisphere shape of the supporting member 322.

The supporting member 322 supports the conversion elements 321. The shape of the supporting member 322 preferably allows arrangement of the conversion elements 321. Specifically, in terms of receiving sensitivity relative to acoustic waves, the supporting member 322 preferably supports the conversion elements 321 such that the conversion elements 321 are arranged on a closed surface surrounding a portion to be examined (a breast). For example, receiving sensitivity of the center of the receiver 32 becomes highest when the conversion elements 321 are arranged on a ball surface such that directions (directionality) of highest receiving sensitivity of the conversion elements 321 direct the center of the ball. However, it is difficult that the conversion elements 321 are arranged on an entire closed surface surrounding the breast.

Therefore, the supporting member 322 may have a recess and the conversion elements 321 may be arranged along a recessed surface of the recess.

The recessed surface may be a curved surface or may be formed by a plurality of planes. However, a center of a curvature of the curved surface (or an approximate curved surface when the recessed surface is configured by a plurality of planes) is preferably located in the certain region (the high sensitivity region). Furthermore, when the conversion elements 321 are arranged along the curved surface, the curved surface preferably has a shape in which the directional axes of at least a number of the conversion elements 321 intersect with the curved surface. Furthermore, the recessed surface is preferably has a shape in which angles defined by surfaces which are perpendicular to directions of highest receiving sensitivity of adjacent conversion elements 321 becomes larger than 0 degree and smaller than 180 degrees.

Since the recessed surface of the supporting member 322 has such a shape, the directional axes of the receiving sensitivity of the conversion elements 321 arranged on the supporting member 322 are converged into the certain region, the receiving sensitivity of the receiver 32 relative to acoustic waves generated from the certain region may be enhanced.

Specifically, the supporting member 322 may have a spherical surface and the conversion elements 321 may be arranged along the spherical surface. Here, the spherical surface includes spherical surfaces other than a surface of a true ball. Specifically, the spherical surface includes a spherical surface having an opening such as a hemisphere face. Furthermore, the spherical surface includes an uneven surface which is still recognized as a spherical surface and a surface of an oval (a shape which is obtained by three-dimensionally expanding an oval and which has a surface thereof formed by a 2D curved surface) which is still recognized as a spherical surface.

The supporting member 322 preferably has a shape in which the directions of highest receiving sensitivity of the conversion elements 321 disposed on the supporting member 322 direct the certain region included in the portion to be examined. Here, in the certain region, receiving sensitivity relative to acoustic waves generated from the certain region of the receiver 32 becomes higher relative to the case where the conversion elements 321 are disposed in parallel to one another. When the subject information obtaining apparatus includes the examination portion holding member, the shape of the supporting member 322 and the arrangement of the conversion elements 321 are set such that the certain region may be located in an examination portion insertion region of the examination portion holding member at a time of measurement.

Furthermore, the conversion elements 321 are preferably disposed on the supporting member 322 such that reception surfaces of the conversion elements 321 are disposed on an inner side of the hemispherical supporting member 322 as described in this embodiment. Here, the hemisphere includes not only a shape obtained by accurately cutting a ball by half but also a shape obtained by cutting out a portion of a ball. Furthermore, the ball includes not only a true ball but also uneven surface which is still recognized as a spherical surface and a surface of an oval (a shape which is obtained by three-dimensionally expanding an oval and which has a surface thereof formed by a 2D curved surface) which is still recognized as a spherical surface.

Furthermore, the conversion elements 321 are arranged on the supporting member 322 such that the conversion elements 321 may be sampled at even intervals in a k-space. Here, data in the k-space may be obtained by performing Fourier transform on data in a real space. Specifically, a coordinate of the real space corresponds to a position coordinate (x, y, z) and an axis in the k-space (kx, ky, kz) corresponds to a special frequency.

For example, the conversion elements 321 are preferably arranged in a spiral manner as disclosed in Japanese Patent No. 4341987. Note that the supporting member 322 has any shape as long as the conversion elements 321 are arranged to form a desired high resolution region.

Furthermore, the light irradiation unit 31 is preferably disposed on the supporting member 322. By this, the constant relationship between a position for receiving acoustic waves and a position for irradiating light is maintained, and accordingly, homogeneous photoacoustic wave information may be obtained. An irradiation area on a breast is restricted by a standard of American National Standards Institute (ANSI). Therefore, to increase quantity of light propagating into a breast, irradiation intensity and the irradiation area are preferably increased. However, the irradiation area is restricted in terms of cost of the light source 5.

Furthermore, according to directionality of the conversion elements 321, when light is irradiated to a region in which receiving sensitivity is small, use efficiency of light quality is low. Therefore, irradiation of light to an entire breast is not efficient. Specifically, when light is irradiated only to a region in which receiving sensitivity is high in the receiver 32, high efficiency is obtained, and therefore, light is preferably moved along with the receiver 32. For example, the subject information obtaining apparatus may further include a light irradiation unit movement mechanism (not illustrated) for moving the light irradiation unit 31. The light irradiation unit movement mechanism differentiates between a position of the light irradiation unit 31 at a time when acoustic waves are received from a first portion to be examined (a left breast) and a position of the light irradiation unit 31 at a time when acoustic waves are received from a second portion to be examined (a right breast).

The movement mechanism 34 moves the receiver 32 and is a two-axis movement mechanism capable of performing 2D scanning in an XY plane. Although the two-axis movement mechanism is illustrated in this embodiment, the movement mechanism 34 may be a three-axis movement mechanism capable of performing 3D scanning in X, Y, and Z directions. The movement mechanism 34 is configured by combining a stage (not illustrated), a linear guide (not illustrated), a feed screw mechanism (not illustrated), a motor (not illustrated) and the like with one another.

In FIG. 1, light irradiated from the light source 5 is guided to a subject by optical components including a lens and a mirror while being processed to have a desired light distribution shape. Furthermore, light irradiated by the light source 5 may be propagated using an optical waveguide such as optical fibers, a bundle optical fiber formed by bundling the optical fibers, or an articulating arm formed by incorporating a mirror and the like in a lens barrel, and the optical waveguide is also considered as the light guiding unit 51. Other examples of the light guiding unit 51 include a mirror which reflects light, a lens which collects light, amplifies light, and changes a shape of light, and a scattering plate which scatters light.

Any optical component may be used as long as light emitted from the light source 5 is irradiated on a breast in a desired shape. Note that light is not preferably collected by a lens but is preferably emitted in a region having a certain area since a large region which receives acoustic waves of a subject may be obtained. Furthermore, when desired pulse light may be directly emitted from the light source 5 to a breast, the photoacoustic apparatus may not include the light guiding unit 51.

Figure 3:
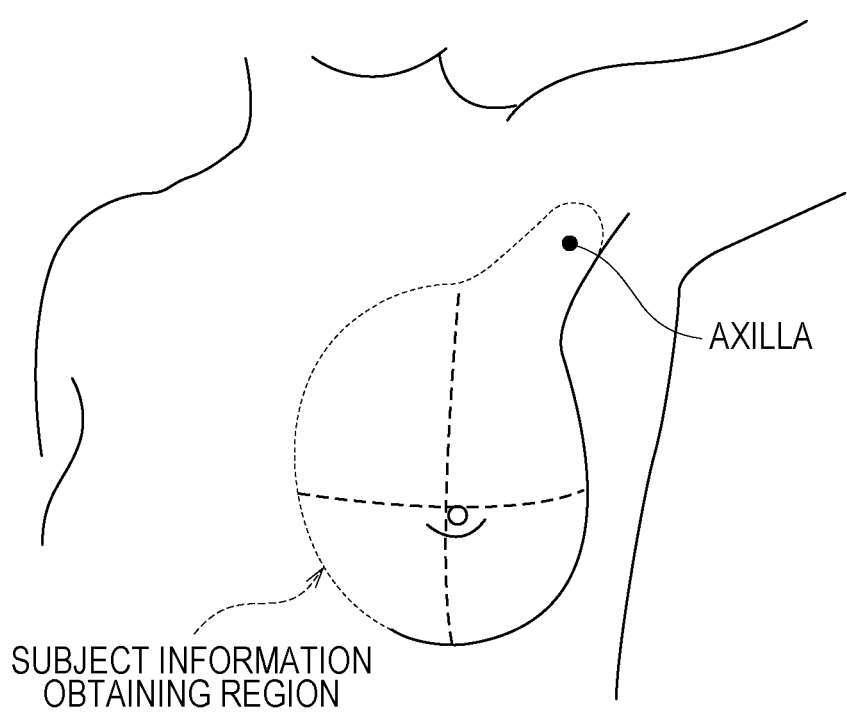
FIG. 3 is a conceptual diagram illustrating a diagnosis region in a breast cancer diagnosis.

FIG. 3 is a diagram schematically illustrating a region from which the subject information obtaining apparatus of this embodiment obtains subject information, that is, a subject information obtaining region. A diagnosis region in a breast cancer diagnosis includes an area of an armpit (axilla) of an examinee. The subject information obtaining apparatus of this embodiment may set the region including the diagnosis region as a subject information obtaining region and set a scanning trajectory corresponding to the region. Different examinees have different diagnosis regions having different shape, different sizes, different positions, and the like. Furthermore, diagnosis regions of right and left breasts are substantially symmetric but are not the same as each other. If a large scanning trajectory is set to cover diagnosis regions of all types of breast, an entire measurement time becomes long, and accordingly, a physical load of an examinee is increased, and an amount of obtainment of data on an unnecessary region is increased. Accordingly, a center position of the scanning trajectory is preferably set for each portion to be examined (each breast).

Furthermore, when the conversion elements 321 are disposed on the supporting member 322 as described in this embodiment, the high sensitivity region is smaller when compared with a case where the conversion elements 321 are arranged in parallel. Accordingly, scanning of the receiver 32 in a position where the high sensitivity region coincides with the unnecessary region is suppressed so that reception of acoustic waves of a portion to be examined may be more efficiently performed.

The controller 2 may obtain a movement amount of the receiver 32 in accordance with an output of a sensor unit 14 (refer to FIG. 1) which detects a position of the receiver 32 and generate a driving signal which is used to move the receiver 32 and which is output to the movement mechanism 34.

The sensor unit 14 is disposed on the movement mechanism 34, for example, detects a position or a movement amount of the receiver 32, and outputs the position or the moving amount to the controller 2. The controller 2 includes a storage unit 2B and a calculation unit 2A. The storage unit 2B may store a size and a shape of a scanning trajectory of the receiver 32, positional data of the receiver 32 detected by the sensor unit 14, and data output from the input unit 8. The calculation unit 2A sets a scanning trajectory of the receiver 32 and a center position of the scanning trajectory using the data stored in the storage unit 2B and obtains a movement amount of the receiver 32 or measurement start position data used to move the receiver 32 to a measurement start position. The controller 2 outputs a driving signal used to move the receiver 32 to the movement mechanism 34 in accordance with a result obtained by the calculation unit 2A. By this, the receiver 32 is moved to the measurement start position by the movement mechanism 34. As described above, the controller 2 controls the movement mechanism 34 so that the movement mechanism 34 changes the center of the scanning trajectory of the receiver 32 in accordance with data input from the input unit 8.

The calculation unit 2A may generate a driving signal to be output to the movement mechanism 34 which is used to control the center of the scanning trajectory, the movement amount of the receiver 32, the measurement start position, and the like in accordance with information (table) on comparison between a scanning trajectory and a center position of the scanning trajectory which correspond to input information and which are stored in the storage unit 2B, instead of calculation of the scanning trajectory and the center position of the scanning trajectory.

Examples of the sensor unit 14 include a potentiometer using an encoder, a variable resistor, or the like and a camera. Examples of the storage unit 2B include storage media such as a ROM, a RAM, and a hard disk. Examples of the calculation unit 2A include a CPU and a Field Programmable Gate Array (FPGA) chip.

Furthermore, the controller 2 may obtain the amount of movement of the receiver 32 from a driving signal supplied to the movement mechanism 34 and store the movement amount in the storage unit 2B as data and may generate a driving signal used to move the receiver 32 to the measurement start position using the stored data instead of an output of the sensor unit 14.

Moreover, the controller 2 may control irradiation of light to a portion to be examined. For example, the controller 2 outputs a driving signal used to control emission of light to the light source 5. The controller 2 may input a driving signal (light irradiation start signal) which starts emission of light to the light source 5 when the receiver 32 is moved to the measurement start position by the movement mechanism 34. Specifically, the controller 2 may input the light irradiation start signal to the light source 5. The light source 5 may include a shutter in a light path and the shutter may be opened and closed in accordance with the light irradiation start signal supplied from the controller 2.

Figure 4:
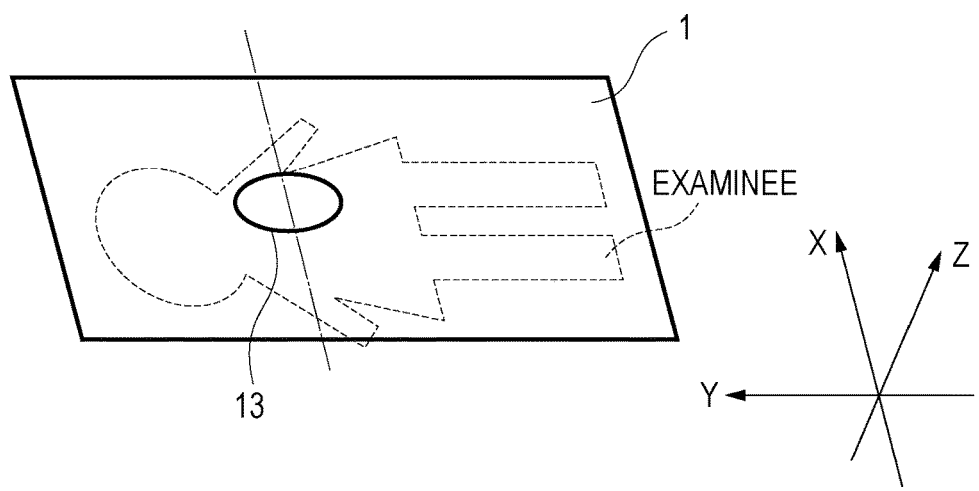
FIG. 4 is a conceptual diagram illustrating a position of an examinee at a time of measurement.
Figure 5:
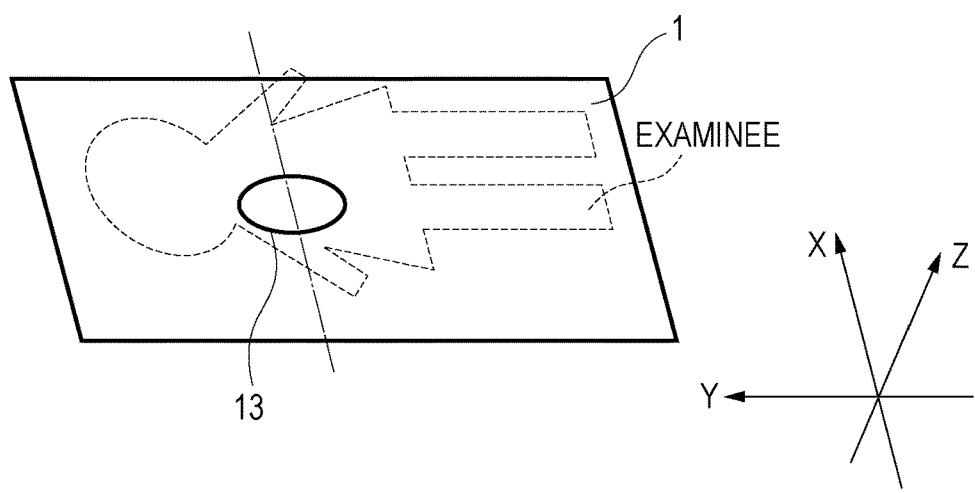
FIG. 5 is a conceptual diagram illustrating a position of an examinee at a time of measurement.

FIGS. 4 and 5 are conceptual diagrams illustrating a position of an examinee at a time of breast measurement.

Figure 6:
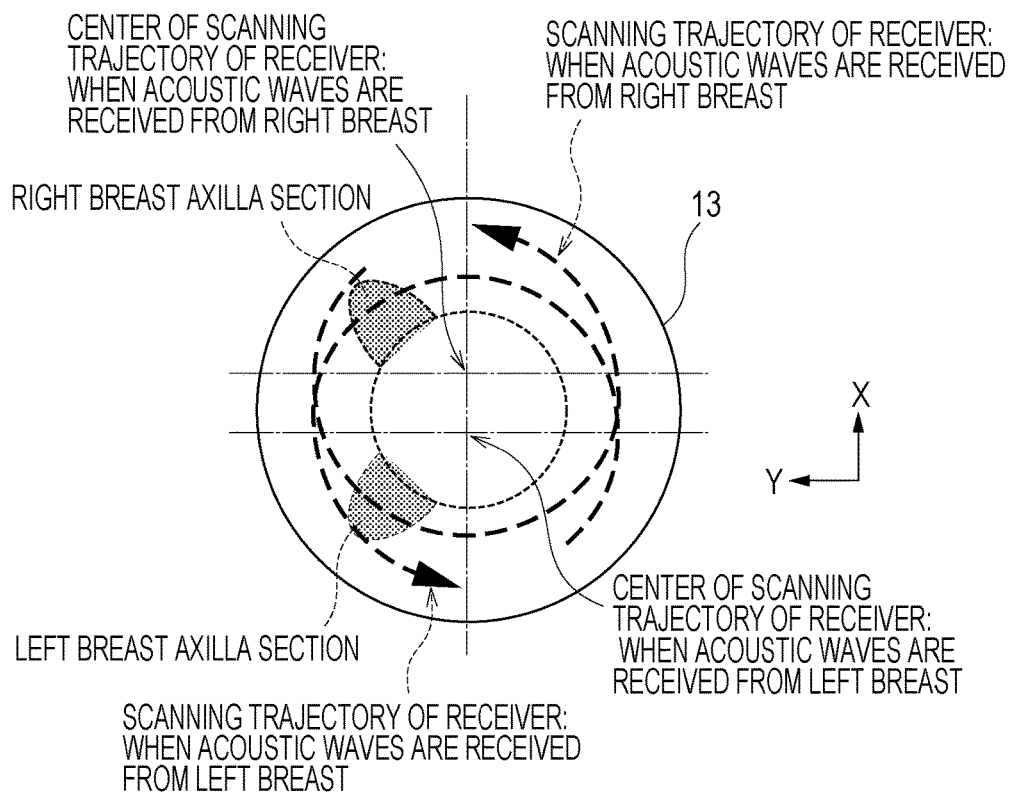
FIG. 6 is a conceptual diagram illustrating scanning trajectories of a receiver.

The examinee moves a body in an X direction and alternately inserts right and left breasts into the breast insertion opening 13 disposed in a certain position. FIG. 6 is a conceptual diagram illustrating subject information obtaining regions and scanning trajectories of the receiver 32 according to this embodiment. When acoustic waves from a portion to be examined are received using circular scanning, a shape of a region formed by tracing an outer periphery of a scanning trajectory in an XY plane is circle and sizes and shapes of such regions for the right and left breasts are the same as each other. The subject information obtaining apparatus of this embodiment shifts centers of the scanning trajectories of the receiver 32 for the right and left breasts from each other in the X direction at the time of measurement. By this, the subject information obtaining regions for the right and left breasts may be adjusted for individual regions.

As described above, since the centers of the scanning trajectories of the receiver 32 for the right and left breasts are different from each other, acoustic waves generated from the information obtaining regions of the right and left breasts may be received using the smaller scanning trajectories when compared with a case where the centers of the scanning trajectories are not differentiated from each other. Specifically, since the centers of the scanning trajectories of the receiver 32 are differentiated for individual portions to be examined, information obtaining regions of the portions to be examined may be obtained by smaller scanning trajectories when compared with the case where the centers of the scanning trajectories are not differentiated. Accordingly, a period of time required for reception of photoacoustic waves may be reduced, and when signal processing and image generation are performed, data corresponding to an unnecessary region may be removed from data to be processed.

Here, in this embodiment, since the shapes of the scanning trajectories of the receiver 32 of the subject information obtaining apparatus is circle, the centers of the scanning trajectories may be differentiated from each other by changing one of the center positions of the circles in a second measurement process. Specifically, for example, information on a center of a scanning trajectory is stored in the storage unit 2B of the controller 2, and the controller 2 sets a position of a region formed by tracing an outer periphery of a scanning trajectory of the receiver 32 such that a center of the scanning trajectory is shifted using the information and outputs a corresponding driving signal to the movement mechanism 34.

Since the position of the region formed by tracing the outer periphery of the scanning trajectory is changed in accordance with a shape, a size, a position, and the like of a portion to be examined, an amount of obtainment of data corresponding to an unnecessary region may be reduced and acoustic waves may be received in a region suitable for each subject.

Note that a scanning trajectory is preferably not changed while measurement is performed a plurality of times, that is, measurement is preferably performed a plurality of times using a predetermined scanning trajectory. Accordingly, since the movement mechanism 34 sets a predetermined scanning trajectory, a size of the scanning trajectory may be limited and a measurement time may be reduced while a configuration of the apparatus is not complicated when compared with a case where the scanning trajectory is changed.

Furthermore, the movement mechanism 34 may execute an arbitrary scanning trajectory selected from among a plurality of predetermined scanning trajectories. In this case, a size of the scanning trajectory may be limited and the measurement time may be reduced while the configuration of the apparatus is not complicated when compared with a case where an arbitrary scanning trajectory is executed.

Although the case where right and left breasts are examined is described in this embodiment, the present invention may be employed in a case where shapes and positions of subject information obtaining regions are different from each other since different examinees are examined.

Although the case where a scanning trajectory of the receiver 32 is circle is described in this embodiment, a scanning trajectory is not limited to this, and a scanning trajectory may be a spiral pattern in an XY plane.

Figure 7:
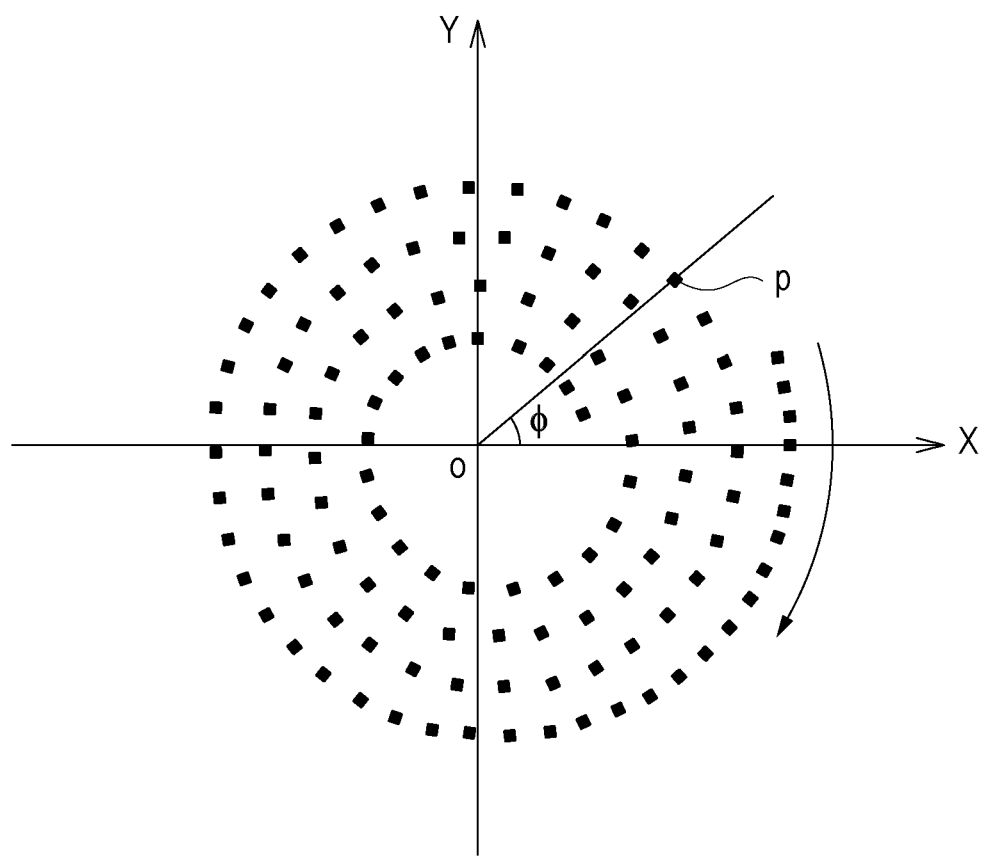
FIG. 7 is a conceptual diagram illustrating a scanning trajectory of a receiver.

A spiral trajectory means a scanning trajectory in which a coordinate of a radial direction relative to a rotation center is moved to an increase direction or a decrease direction. FIG. 7 is a conceptual diagram illustrating a scanning trajectory of the receiver 32 of this embodiment and is a diagram schematically illustrating movement of a spiral trajectory. An origin O of FIG. 7 is a center of the scanning trajectory of the receiver 32 at a time of measurement and black points represent positions of the receiver 32 at different timings at the time of the measurement. The receiver 32 moves along the positions of the black points. A point P denotes a certain point on the scanning trajectory of the receiver 32. When a position coordinate (x, y) of the point P is represented in a polar coordinate system, Expression (1) is obtained.

$$x = r(t) \cos \Phi$$

$$y = r(t) \sin \Phi \qquad \text{Expression (1)}$$

Here, "r(t)" denotes a coordinate of the radial direction (a radius of movement) and "$\Phi$" denotes an angle defined by an X axis and a line extending from the origin toward the point P. In this embodiment, the receiver 32 is moved such that the coordinate r(t) of the radial direction on the scanning trajectory of the receiver 32 is changed to an increase direction or a decrease direction.

Furthermore, the movement mechanism 34 preferably moves the receiver 32 from an outside of a movement plane taking acceleration toward the origin into consideration. Specifically, when acceleration in an initial stage of movement is large, the entire apparatus may be considerably shaken and the shake may affect measurement. Therefore, when movement is started from an outer periphery in which acceleration toward the origin is small, and thereafter, the movement is continued toward an inner periphery, the shake of the apparatus is suppressed.

Also in this case, a center of the scanning trajectory may be changed by changing a center position of a spiral shape in a second measurement process.

Accordingly, for example, information on the center position of the scanning trajectory may be stored in the storage unit 2B of the controller 2, and the controller 2 may set a measurement position of the receiver 32 such that a center of a scanning trajectory is shifted using the information and output a corresponding driving signal to the movement mechanism 34.

As described above, since a center of a scanning trajectory is changed in accordance with a shape, a size, and a position of a portion to be examined, an amount of obtainment of data corresponding to an unnecessary region may be reduced and acoustic waves may be received in an appropriate region for each subject.

Figure 8:
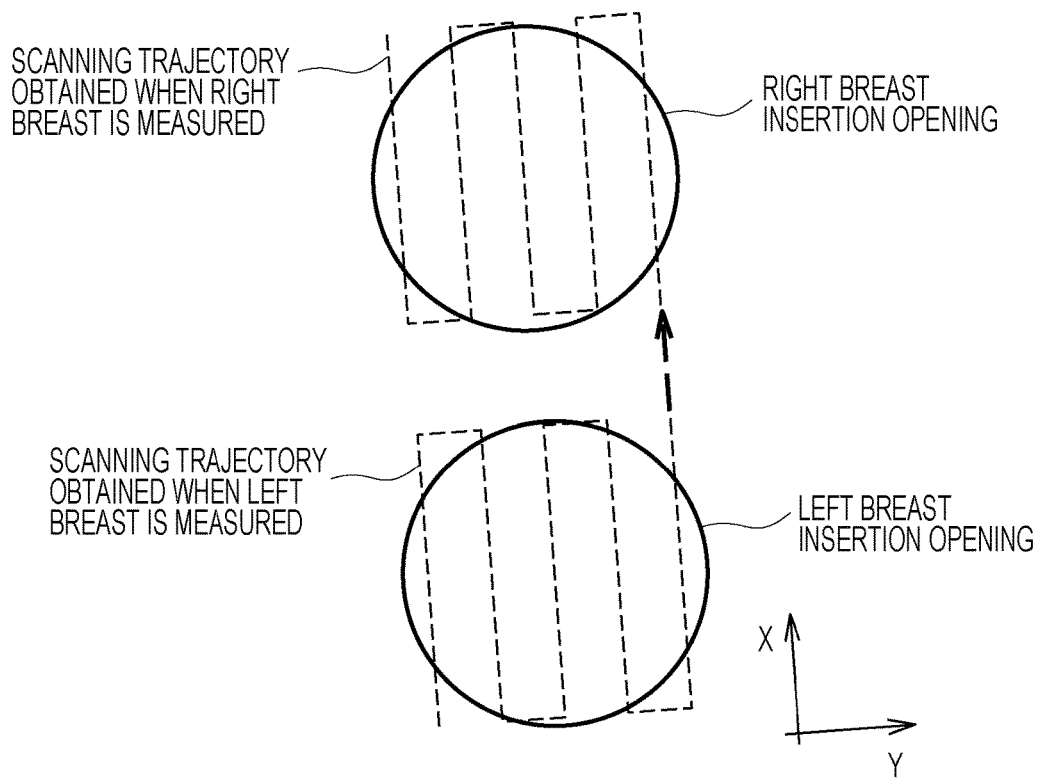
FIG. 8 is a conceptual diagram illustrating a scanning trajectory of a receiver.

Furthermore, a scanning trajectory of the receiver 32 may be substantially a straight line. FIG. 8 is a conceptual diagram illustrating a scanning trajectory of the receiver 32 when a left breast is measured before a right breast is measured. For example, the receiver 32 receives acoustic waves while moving in an X direction (a main scanning direction), and when reaching an end of a subject information obtaining region, the receiver 32 moves in an Y direction (a sub-scanning direction). Subsequently, the receiver 32 receives acoustic waves while moving in the X direction. Here, the receiver 32 moves in a direction opposite to the preceding scanning in the X direction. When reaching an end of the subject information obtaining region, the receiver 32 moves in the Y direction again. This process is repeatedly performed so that acoustic waves are received from the left breast.

Next, the receiver 32 is moved in a scanning direction of a time when the measurement of the left breast is terminated, and when reaching a subject information obtaining region of the right breast, the receiver 32 starts measurement of the right breast. Then measurement is performed on the right breast using the scanning trajectory illustrated in FIG. 8.

Note that sub-scanning is preferably performed with such a movement amount that a high resolution region in a preceding main scanning and a high resolution region in a succeeding main scanning overlap with each other. By this, variation of resolution in the portion to be examined may be reduced.

As described above, unlike a circle and a spiral, when the scanning trajectory has a shape which does not clearly have a center, a center of a gravity of a region formed by tracing outermost periphery of the scanning trajectory may be set as a center of the scanning trajectory.

In the foregoing description, the case where acoustic waves are received while the receiver 32 is moved in the XY plane is described as an example. However, the movement mechanism 34 may cause the receiver 32 to perform scanning in a Z direction (a direction parallel to a direction in which a breast is inserted in this embodiment) which is perpendicular to the XY plane. Since the receiver 32 also scans in the Z direction, the high resolution region is also moved in the Z direction, and accordingly, measurement may be performed with high accuracy in a larger region.

Figure 9:
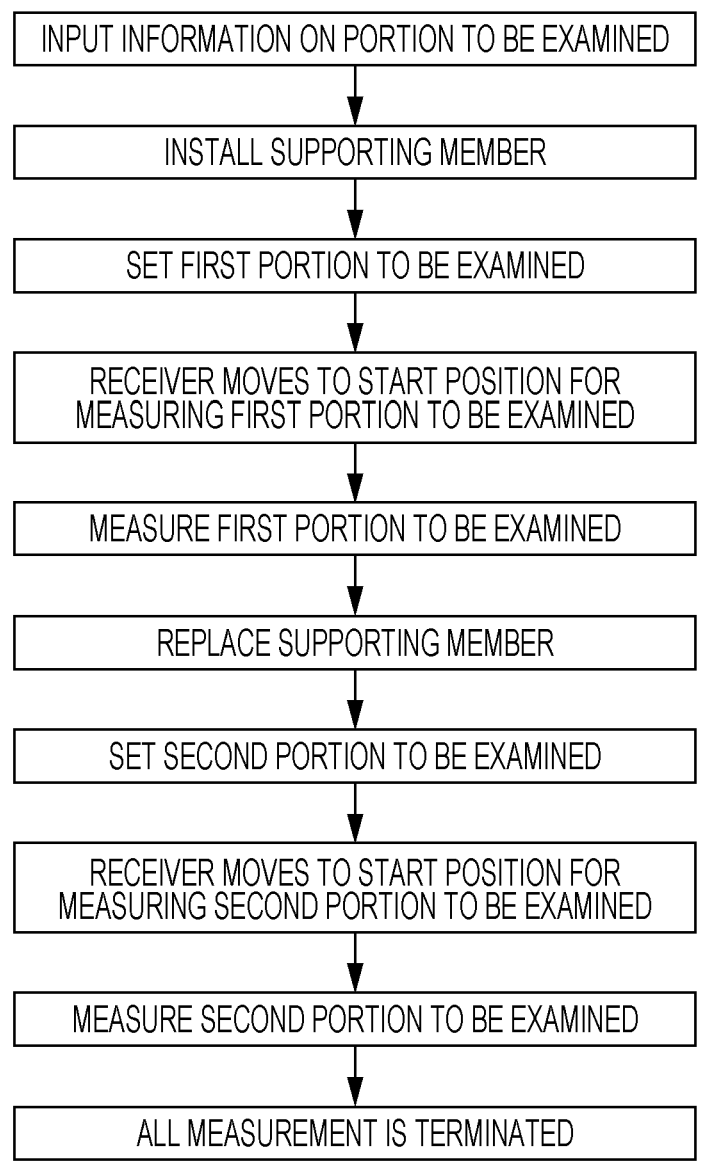
FIG. 9 is a diagram illustrating a flow of obtainment of subject information.

FIG. 9 is a diagram illustrating a flow of obtainment of subject information according to this embodiment. An operator installs the holding member 11 suitable for a breast which is a target of obtainment of information before reception of acoustic waves. The holding member 11 may be replaceable and may be fixedly attached. When the holding member 11 has been installed in advance, this step may be omitted. Here, the case where the holding member 11 is installed before information on a target portion to be examined is input is described in this embodiment as an example. However, the holding member 11 may be installed after the information on the target portion to be examined is input.

Information (right or left, a position, a shape, and the like) on a portion to be examined (a breast) which is a target of information obtainment may be input by the operator to the input unit 8 or an output of the examination portion detector 12 may be input as the information to the input unit 8. When the output of the examination portion detector 12 is used, input of the information on the portion to be examined (the target breast) performed by the operator may be omitted. After the first portion to be examined (one of the breasts) is positioned, the receiver 32 is moved to the measurement start position by the movement mechanism 34 and starts reception of acoustic waves. After measurement by a set scanning trajectory is terminated, the operator replaces the holding member 11 by another one where appropriate.

Thereafter, the second portion to be examined (the other of the breasts) is positioned on the holding member 11, the receiver 32 is moved to a position for receiving acoustic waves generated from the second portion to be examined, and the subject information obtaining apparatus starts reception of acoustic waves generated from the second portion to be examined.

In this case, the subject information obtaining apparatus may not input information on a breast to be measured. For example, processes to be performed on the two breasts (the right and left breasts in this embodiment) which are targets of consecutive measurement processes and information on the processes are stored in the storage unit 2B of the controller 2. The controller 2 reads information on the second breast from the storage unit 2B in accordance with the information on the portion to be examined which is input before the measurement. The controller 2 outputs a signal for causing the receiver 32 to move to the measurement start position to the movement mechanism 34 in accordance with the read information. The receiver 32 starts reception in the measurement start position set by the controller 2 so as to receive acoustic waves generated by the other breast.

Furthermore, the subject information obtaining apparatus may be configured such that, after one of the breasts is measured, the operator inputs information (right or left, a position, a shape, a size, and the like) on the other of the breasts. Furthermore, the subject information obtaining apparatus may be configured such that an output of the examination portion detector 12 associated with the other breast is input to the input unit 8.

In this embodiment, although the case where the examination portion holding member is installed is described as an example, the examination portion holding member may not be installed and the subject information obtaining apparatus may be configured such that a breast protruding downward is inserted into the breast insertion opening 13 and is directly immersed into the adjustment member 35.

In this way, since a position of a region formed by tracing an outer periphery of a scanning trajectory of the receiver 32 at a time of measurement is changed for each portion to be examined, information obtaining regions of the portions to be examined may be covered by smaller scanning trajectories when compared with a case where the position of the region formed by tracing the outer periphery of the scanning trajectory is not changed. Accordingly, a period of time required for receiving photoacoustic waves may be reduced, and when signal processing and image generation are to be performed, data corresponding to an unnecessary region may be removed from data to be processed.

Second Embodiment

In a second embodiment, a case where a subject information obtaining apparatus includes a subject supporting member having a plurality of openings and a plurality of receivers corresponding to the openings will be described as an example. Specifically, a subject information obtaining apparatus including a subject supporting member (a bed 1) having two openings (breast insertion openings 13) for inserting portions to be examined and two examination portion holding members will be described as an example. Note that configurations and operations the same as those of the first embodiment are denoted by reference numerals the same as those of the first embodiment, and detailed descriptions thereof are omitted.

Figure 10:
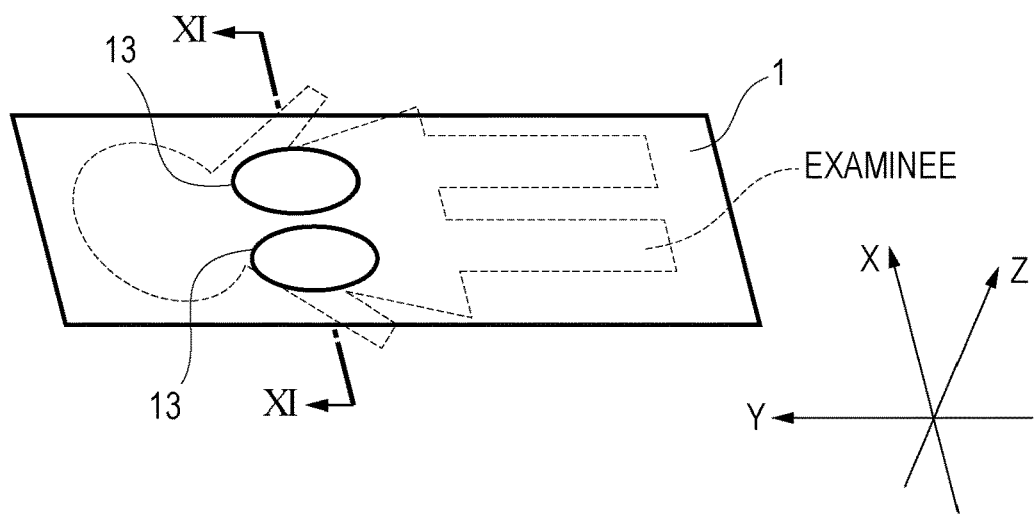
FIG. 10 is a conceptual diagram illustrating a position of an examinee at a time of measurement.

FIG. 10 is a conceptual diagram illustrating a position of an examinee at a time when portions to be examined are measured. The subject information obtaining apparatus of this embodiment is configured such that the two breast insertion openings 13 which are subject insertion openings are disposed on the bed 1 which is a subject supporting unit so that both of right and left breasts may be simultaneously inserted in the breast insertion openings 13. The breast insertion openings 13 are configured so as to allow both the breasts to be simultaneously inserted, and therefore, only a large insertion opening may be disposed. In this case, it is preferable that both the breasts are simultaneously supported by a breast supporting member (not illustrated) so that both the breasts do not sink too much. A holding member 11 may be configured by a single member or may be configured by different members for the right and left breasts.

Figure 11:
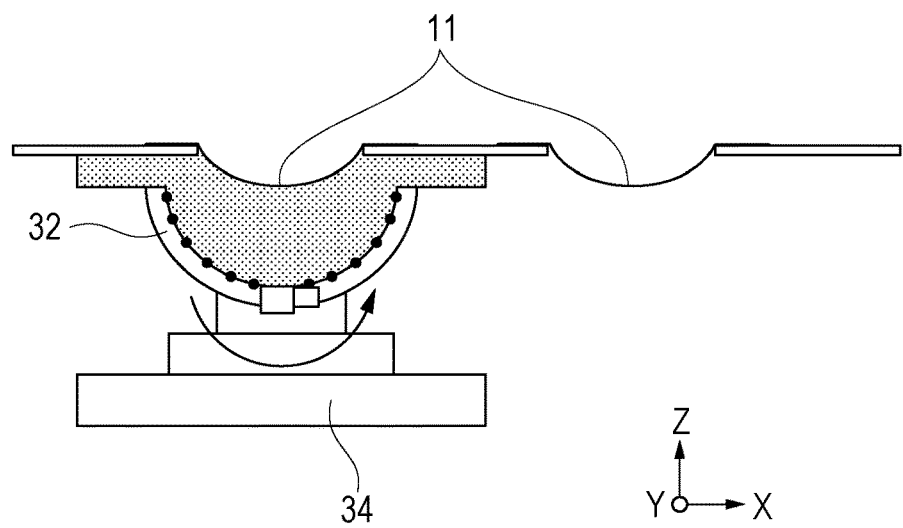
FIG. 11 is a conceptual diagram illustrating the subject information obtaining apparatus viewed from a cross sectional surface along a line XI-XI of FIG. 10.

FIG. 11 is a conceptual diagram of the subject information obtaining apparatus viewed from a cross sectional surface along a line XI-XI of FIG. 10. A movement mechanism 34 of this embodiment causes a receiver 32 to scan a range required for receiving acoustic waves of both the right and left breasts. Specifically, the movement mechanism 34 has a larger movement stroke in an X direction when compared with the first embodiment. A controller 2 (FIG. 1) is constituted by a CPU or the like, and controls a method for controlling the movement mechanism 34 in accordance with information input to an input unit 8 (FIG. 1) at a time of measurement.

The input unit 8 inputs information on a type (right or left), a position, a size, a shape, and the like of a breast. As an input method, the operator may directly input the information in the input unit 8. Furthermore, information on a portion to be examined (a target breast) may be automatically input to the input unit 8 by inputting an output of an examination portion detector 12 (a target breast detector) (FIG. 1) to the input unit 8. With these configurations, the operator is not required to directly input a type of breast and the like, and wrong subject portion information generated by an input error of the operator may be prevented from being obtained.

Figure 12:
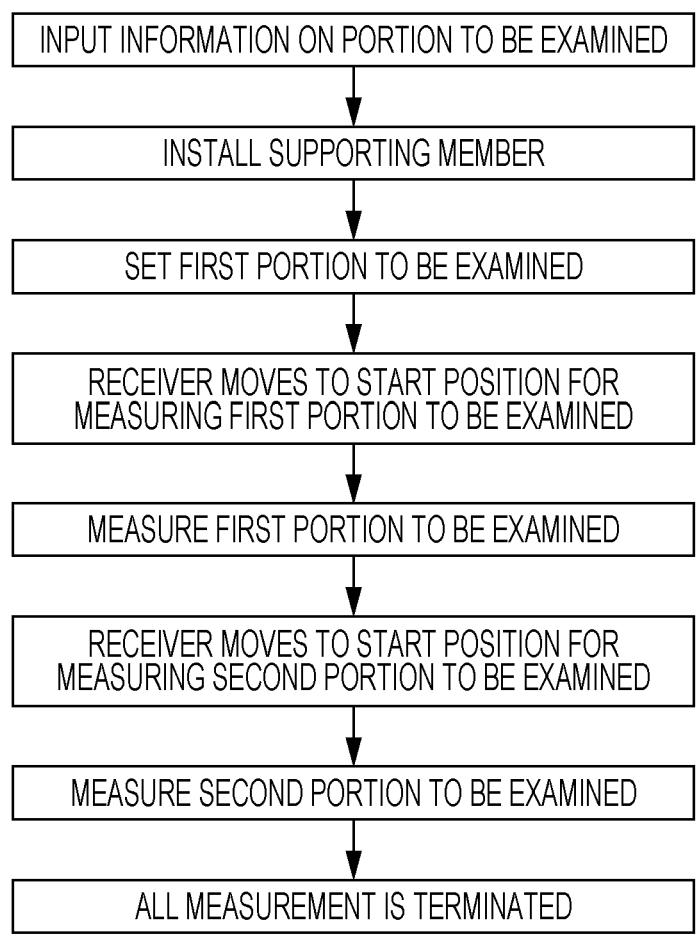
FIG. 12 is a diagram illustrating a flow of obtainment of subject information.

FIG. 12 is a diagram illustrating a flow of obtainment of subject information according to this embodiment. The operator installs a supporting member corresponding to a first portion to be examined (one of the breasts) which is a target which generates acoustic waves to be received and inputs information on the first portion to be examined (a type of breast, for example). After a breast is set in an examination portion holding member, the receiver 32 is moved to a measurement start position by the movement mechanism 34 and reception of acoustic waves from the first portion to be examined is started. After the acoustic waves from the first portion to be examined are received, the receiver 32 is moved to a measurement start position for a second portion to be examined (the other of the breasts) by the movement mechanism 34. Thereafter, the receiver 32 receives acoustic waves from the second portion to be examined.

The subject information obtaining apparatus of this embodiment is capable of measuring both the breasts when the examinee once sets the breasts in a prone position, and therefore, a load of position adjustment of the examinee generated when the breasts to be examined are switched from one to another may be reduced.

Although the case where the two examination portion holding members are disposed is described as an example in this embodiment, the examination portion holding members may not disposed and breasts protruding downward may be inserted into breast insertion openings 13 and directly immersed into the adjustment member 35.

Figure 13:
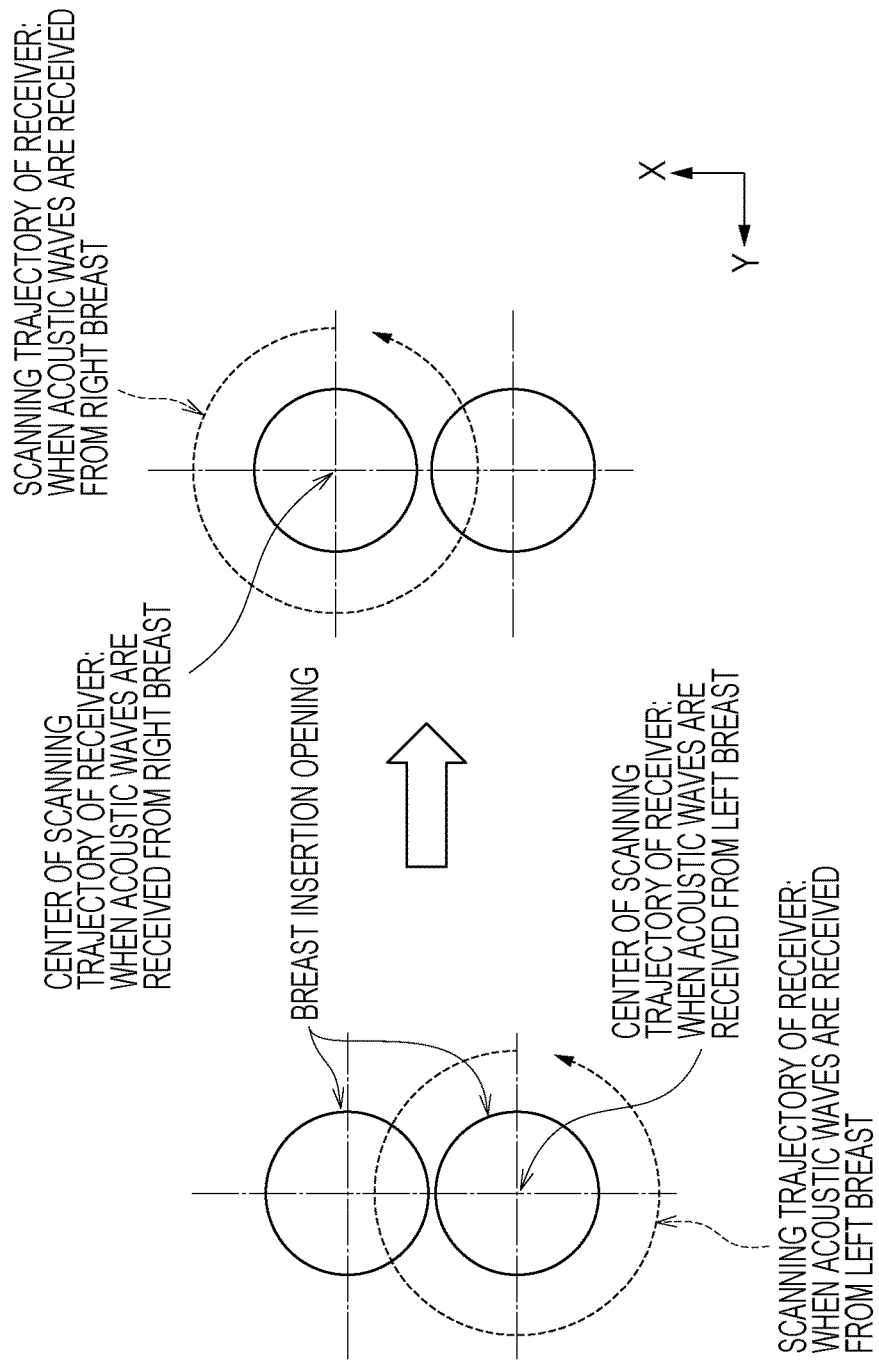
FIG. 13 is a conceptual diagram illustrating scanning trajectories of a receiver.

FIG. 13 is a conceptual diagram schematically illustrating scanning trajectories of the receiver 32 according to this embodiment. In this embodiment, a case where the scanning trajectories have a circle shape will be described.

The subject information obtaining apparatus of this embodiment receives acoustic waves of one of the breasts by performing scanning by the receiver 32 along a scanning trajectory having a first rotation center. Thereafter, scanning is performed along a scanning trajectory having a second rotation center obtained by shifting the first rotation center of the scanning trajectory of the receiver 32 in an X direction so that acoustic waves of the other of the breasts are received. A size and a shape of a region formed by tracing an outer periphery of the scanning trajectory of the right breast are the same as those of the left breast. By this, since the centers of the scanning trajectories of the receiver 32 for the right and left breasts are different from each other and positions of the regions formed by tracing the outer peripheries of the scanning trajectories are different from each other, a period of time used to obtain subject information may be reduced. Furthermore, an amount of obtainment of data of an unnecessary region may be reduced when signal processing is performed and an image is generated. Furthermore, when a scanning trajectory is controlled such that a region formed by tracing an outer periphery of the scanning trajectory of the receiver 32 is changed using information input to the input unit 8, a more optimum scanning region may be obtained. For example, the controller 2 may read a scanning trajectory corresponding to the information input to the input unit 8 from data on a plurality of scanning trajectories stored in the controller 2. Note that an adjustment mechanism (not illustrated) which adjusts positions of the breast insertion openings 13 or a breast supporting member (not illustrated) in accordance with positions of breasts of an examinee may be provided. The adjustment mechanism may be electrically operated or manually operated by the operator. With this configuration, a load of the examinee may be reduced when positioning of breasts is performed. Furthermore, an examination portion detector 12 (FIG. 1) detects positions of the breast insertion openings 13 or a position of the holding member 11 and the controller 2 outputs a driving signal to the movement mechanism 34 so that centers of scanning trajectories of the receiver 32 are differentiated depending on targets generating acoustic waves to be received.

In this way, since a center of a scanning trajectory of the receiver 32 is changed for each portion to be examined at a time of measurement, information obtaining regions of portions to be examined may be covered by smaller scanning trajectories when compared with a case where a center of a scanning trajectory is not changed. Accordingly, a period of time used for reception of acoustic waves may be reduced, and when signal processing and image generation is performed, data corresponding to an unnecessary region may be removed from data to be processed. Furthermore, portions to be examined are not changed to other portions, a load of the examinee may be reduced, and a period of time to be used for changing portions to be examined may be removed from a period of time used to receive acoustic waves.

Third Embodiment

In a third embodiment, a case where a subject information obtaining apparatus includes a plurality of examination portion holding members and a plurality of receivers corresponding to the examination portion holding members will be described as an example. Specifically, a subject information obtaining apparatus including a subject supporting member (a bed 1) having two openings (breast insertion openings 13) for inserting portions to be examined, two examination portion holding members, and two receivers 32 will be described as an example. For example, this embodiment may be employed in a case where reception of acoustic waves of both of breasts of an examinee A is performed, and thereafter, reception of acoustic waves of both of breasts of an examinee B is performed. Note that configurations and operations the same as those of the first embodiment or the second embodiment are denoted by reference numerals the same as those of the first embodiment or the second embodiment, and detailed descriptions thereof are omitted.

Figure 14:
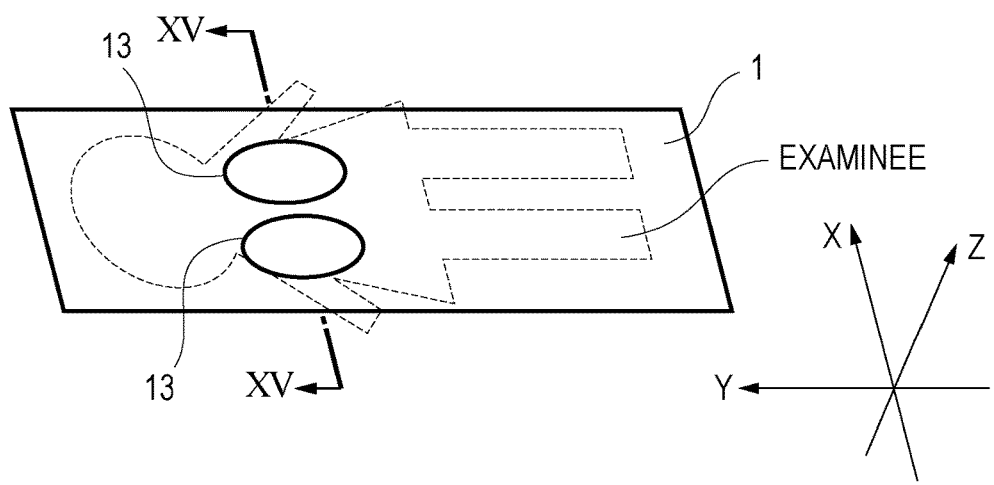
FIG. 14 is a conceptual diagram illustrating a position of an examinee at a time of measurement.

FIG. 14 is a conceptual diagram illustrating a position of an examinee at a time of measurement. The subject information obtaining apparatus of this embodiment is configured such that the two breast insertion openings 13 (openings) are disposed on the bed 1 which is a subject supporting unit so that both of right and left breasts are simultaneously inserted in the breast insertion openings 13. The breast insertion openings 13 are configured so as to allow both the breasts to be simultaneously inserted, and therefore, only a large insertion opening may be disposed. In this case, it is preferable that both the breasts are simultaneously supported by a breast supporting member (not illustrated) so that both of the breasts do not sink too much. A holding member 11 (an examination portion holding member) may be configured by a single member or may be configured by different members for the right and left breasts.

In this embodiment, although the case where the two examination portion holding members are installed is described as an example, the examination portion holding members may not be installed and the subject information obtaining apparatus may be configured such that breasts protruding downward are inserted into the breast insertion openings 13 and are directly immersed into an adjustment member 35.

Figure 15:
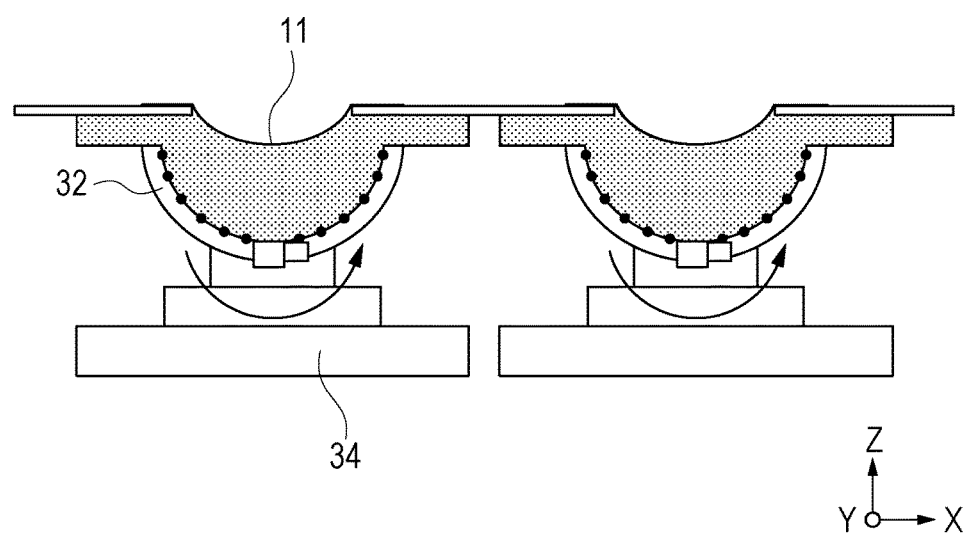
FIG. 15 is a conceptual diagram illustrating the subject information obtaining apparatus viewed from a cross sectional surface along a line XV-XV of FIG. 14.

FIG. 15 is a conceptual diagram illustrating the subject information obtaining apparatus viewed from a cross sectional surface along a line XV-XV of FIG. 14. In this embodiment, the two receivers 32 and two movement mechanisms 34 are provided. Acoustic waves from the right and left breasts are simultaneously received using the two receivers 32 and the two movement mechanism 34. The controller 2 (FIG. 1) is configured such that control signals of the receivers 32 are input to the movement mechanisms 34 in accordance with an input of an input unit 8 (FIG. 1) at a time of measurement. Examples of information input to the input unit 8 include types (right and left), shapes, positions, and the like of the breasts. An operator may directly input the information to the input unit 8 as an input method. Furthermore, information on portions to be examined (target breasts) may be automatically input to the input unit 8 by inputting an output of the examination portion detector 12 (FIG. 1) to the input unit 8. With these configurations, the operator is not required to directly input types of the breasts and the like, and wrong subject portion information generated by an input error of the operator is prevented from being obtained.

Figure 16:
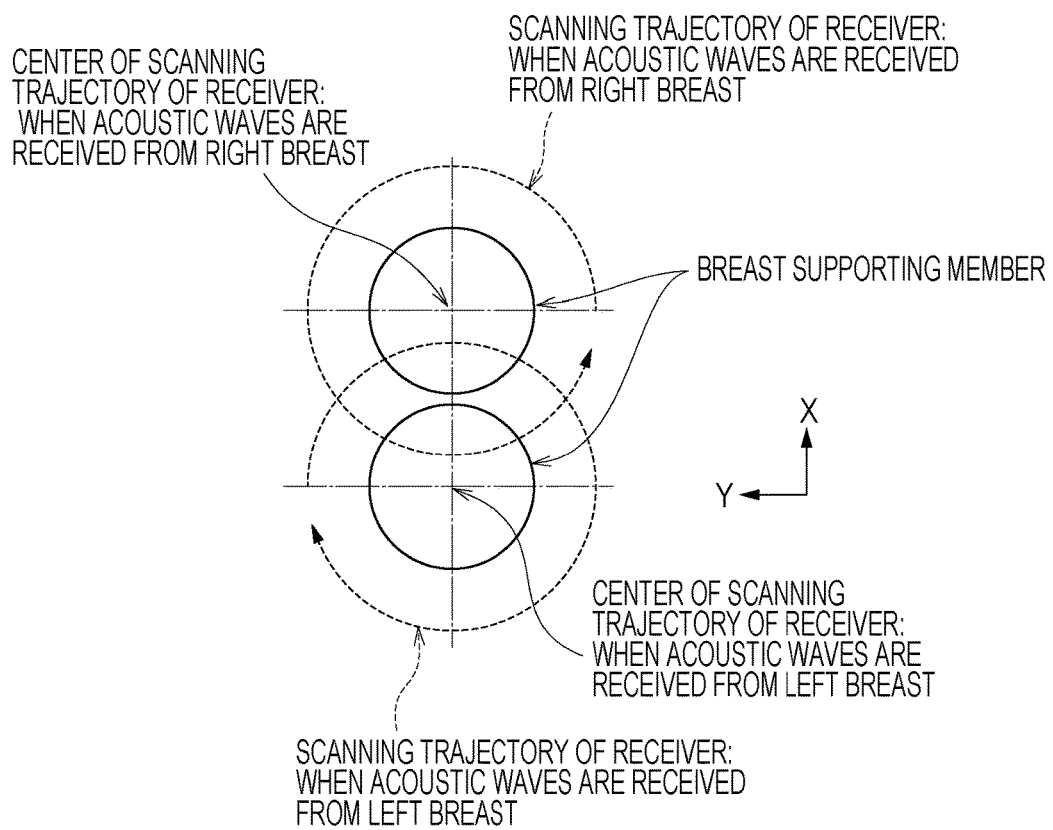
FIG. 16 is a conceptual diagram schematically illustrating scanning trajectories of receivers.

FIG. 16 is a conceptual diagram illustrating scanning trajectories of the receivers 32 according to this embodiment. Acoustic waves from the right breast are received by performing scanning using a first receiver 32 while acoustic waves from the left breast are received by performing scanning using a second receiver 32. The controller 2 determines positions (measurement start positions) where reception of acoustic waves by the receivers 32 is started in accordance with information input to the input unit 8 (FIG. 1) by the operator or information input to the input unit 8 from the examination portion detector 12 (FIG. 1). Specifically, the controller 2 is configured to input signals associated with positions where reception of acoustic waves is started by the receivers 32 for two portions to be examined (the right and left breasts in this embodiment) to the movement mechanism 34. The receivers 32 are moved to the measurement starting positions by the movement mechanisms 34, and thereafter, reception of acoustic waves from the portions to be examined is started. Specifically, center positions of scanning trajectories of the receivers 32 are changed from positions of a preceding reception, and regions formed by tracing outer peripheries are moved to appropriate positions for individual portions to be examined. Accordingly, since reception of acoustic waves from an unnecessary region may be reduced, a period of time used to receive acoustic waves may be reduced, and an amount of data to be processed may be reduced when signal processing is performed and an image is generated.

Furthermore, the subject information obtaining apparatus of this embodiment may simultaneously receive acoustic waves from the two breasts, and accordingly, a period of time used to receive the acoustic waves may be reduced and a load of an examinee may be reduced.

Furthermore, since the scanning trajectories of the receivers 32 are controlled using the information input to the input unit 8, scanning ranges may be further optimized. For example, the controller 2 may read scanning trajectories corresponding to the information input to the input unit 8 from data of a plurality of scanning trajectories stored in the controller 2. Note that an adjustment mechanism (not illustrated) which adjusts a position of the breast insertion openings 13 or supporting members 11 (FIG. 1) in accordance with positions of the breasts of the examinee may be provided. The adjustment mechanism may be electrically operated or manually operated by the operator. With these configurations, a load of the examinee may be reduced when positioning of the breasts is performed.

Furthermore, the examination portion detector 12 (FIG. 1) detects positions of the breast insertion openings 13 or the supporting members 11 so that centers of the scanning trajectories of the receivers 32 are changed in accordance with targets generating acoustic waves to be received. By this, positions of regions formed by tracing outer peripheries of the scanning trajectories of the receivers 32 may be changed in accordance with targets generating acoustic waves to be received. Since different examinees have different shapes of the targets generating acoustic waves to be received, when scanning trajectories of the receivers 32 are set such that the scanning trajectories cover entire regions of the targets generating acoustic waves to be received, the scanning trajectories become large. However, change of the positions of the centers of the scanning trajectories of the receivers 32 enables reception of acoustic waves in positions corresponding to the targets generating acoustic waves to be received while enlargement of the scanning trajectories is suppressed.

In this embodiment, when the scanning trajectories of the receivers 32 have a circle shape, phases and directions of rotations of the two receivers 32 are preferably coincide with each other, for example. By this scanning, interference between the two receivers 32 may be avoided. Furthermore, as another example, a configuration in which rotation directions of the two receivers 32 are opposite to each other as illustrated in FIG. 16 and phases thereof are shifted by 180 degrees is also preferable. By this scanning, interference between the two receivers 32 may be avoided, and furthermore, a load in a Y direction applied to the subject information obtaining apparatus due to acceleration of the receivers 32 may be cancelled. Accordingly, vibration of the subject information obtaining apparatus may be suppressed.

The centers of the scanning trajectories of the receivers 32 are changed at measurement for each portion to be examined, and therefore, regions in which information on portions to be examined is obtained may be covered by smaller scanning trajectories when compared with a case where the centers of the scanning trajectories are not changed. Accordingly, a period of time used for reception of acoustic waves may be reduced, and when signal processing and image generation are performed, data corresponding to an unnecessary region may be removed from data to be processed. Furthermore, since a process of changing a portion to be examined to another portion is omitted, a load of the examinee may be reduced, and a period of time to be used for changing a portion to be examined may be removed from a period of time in which acoustic waves are received. Furthermore, since receptions of acoustic waves from two portions to be examined may be simultaneously performed, a period of time used to receive the acoustic waves is reduced and a load of the examinee is also reduced.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-227240, filed Oct. 31, 2013, which is hereby incorporated by reference herein in its entirety.

What is claimed is:

1. A subject information obtaining apparatus comprising:
    a receiver having a plurality of conversion elements which receive acoustic waves and output reception signals and a supporting member that supports the plurality of conversion elements such that directional axes of the plurality of conversion elements gather;
    a movement mechanism configured to move the receiver; and
    a controller configured to control a movement of the movement mechanism to move the receiver along a scanning trajectory by moving the receiver relative to an examined portion of the subject, a center position of the scanning trajectory being a center of gravity of a region formed by tracing an outer periphery of the scanning trajectory,
    wherein the controller controls the movement mechanism so that in a case in which the examined portion lies in the left side of the body, the center position of the scanning trajectory of the receiver is offset from the center position of the scanning trajectory of the receiver from where the center position of the scanning trajectory of the receiver would be in a case the examined portion lies in the right side of the body.

2. The subject information obtaining apparatus according to claim 1, wherein
    the controller includes a storage unit capable of storing data on a size and a shape of the scanning trajectory, data on a position of the receiver, and information input from an input unit and a calculation unit which calculates a movement amount or a measurement start position of the receiver in accordance with the data stored in the storage unit.

3. The subject information obtaining apparatus according to claim 2, wherein
    the controller controls the movement mechanism based on a result of the calculation performed by the calculation unit.

4. The subject information obtaining apparatus according to claim 1, wherein
    the controller controls the movement mechanism to start emission of light to a light source after the receiver is moved to a measurement start position by the movement mechanism.

5. The subject information obtaining apparatus according to claim 1, further comprising
    an examination portion detector configured to detect a portion to be examined,
    wherein the controller controls the movement mechanism so that the center position of the scanning trajectory of the receiver is changed in accordance with an output of the examination portion detector.

6. The subject information obtaining apparatus according to claim 1, further comprising:
    a light source configured to generate light; and
    a light irradiation unit configured to emit light guided from the light source.

7. The subject information obtaining apparatus according to claim 6, wherein
    the light irradiation unit is disposed in the supporting member.

8. The subject information obtaining apparatus according to claim 6, further comprising:
    a light irradiation unit movement mechanism configured to move the light irradiation unit,
    wherein the light irradiation unit movement mechanism changes a position to which light is irradiated for each examined portion.

9. The subject information obtaining apparatus according to claim 1, further comprising:
    a subject supporting member having a plurality of openings to which portions to be examined are inserted.

10. The subject information obtaining apparatus according to claim 1, further comprising:

a plurality of supporting members configured to individually support portions to be examined.

11. A driving method of a subject information obtaining apparatus having a receiver that includes therein a plurality of conversion elements and a supporting member that supports the plurality of conversion elements such that directional axes of the conversion elements gather, and a moving mechanism configured to move the receiver relative to the subject, the driving method comprising:

Moving the receiver, using the moving mechanism, relative to an examined portion of the body along a scanning trajectory, a center position of the scanning trajectory being a center of gravity of a region formed by tracing an outer periphery of the scanning trajectory; and offsetting the center position of the scanning trajectory, in a case in which the examined portion lies in the left side of the body, from where the center of the scanning trajectory would be in a case the examined portion lies in the right side of the body.

12. The subject information obtaining apparatus according to claim 1, wherein the scanning trajectory is a spiral.

13. The subject information obtaining apparatus according to claim 12, wherein the controller controls the movement mechanism to move the receiver along the spiral in an inward direction.

14. The subject information obtaining apparatus according to claim 1, further comprising a holding member that holds the subject.

15. The subject information obtaining apparatus according to claim 1, further comprising a camera configured to capture an image of the object.

16. The driving method according to claim 11, wherein the scanning trajectory is a spiral.

17. The driving method according to claim 16, further comprising controlling the movement mechanism to move the receiver along the spiral in an inward direction.

18. A subject information obtaining apparatus comprising:

a pair of receivers each having a plurality of conversion elements which receive acoustic waves and output reception signals and a supporting member that supports the plurality of conversion elements such that directional axes of the plurality of conversion elements gather;

a movement mechanism configured to move the pair of receivers; and a controller configured to control a movement of the movement mechanism to move the pair of receivers along mutually different scanning trajectories by moving the receiver relative to an examined portion of the subject, wherein the mutually different scanning trajectories having an overlapping portion, and the controller controls the moving mechanism such that the pair of receivers pass the overlapping portion at different timings.

19. The subject information obtaining apparatus according to claim 18, wherein the controller controls the movement mechanism so that the pair of receivers each moves along a mutually different circular scanning trajectory, wherein positions of the pair of receivers relative to a center of the circular trajectory coincide with each other.

20. The subject information obtaining apparatus according to claim 19, wherein the controller controls the movement mechanism so that the pair of receivers each moves along a corresponding one of the circular trajectories in mutually opposite directions.

21. The subject information obtaining apparatus according to claim 1, further comprising:

an input unit configured to input information on a portion to be examined, wherein the controller controls the movement mechanism so that the center position of the scanning trajectory of the receiver is changed in accordance with the information on the portion to be examined input from the input unit.

* * * * *